United States Patent
Bienvenu

(10) Patent No.: US 10,583,274 B2
(45) Date of Patent: Mar. 10, 2020

(54) EXTREMITY STABILIZATION SYSTEM FOR MEDICAL PROCEDURES

(71) Applicant: Ansley Lauren Bienvenu, Youngsville, LA (US)

(72) Inventor: Ansley Lauren Bienvenu, Youngsville, LA (US)

( * ) Notice: Subject to any disclaimer, the term of this patent is extended or adjusted under 35 U.S.C. 154(b) by 0 days.

(21) Appl. No.: 16/350,583

(22) Filed: Nov. 28, 2018

(65) Prior Publication Data
US 2019/0232023 A1  Aug. 1, 2019

Related U.S. Application Data

(60) Provisional application No. 62/593,459, filed on Dec. 1, 2017.

(51) Int. Cl.
*A61M 25/02*  (2006.01)
*A61F 5/37*  (2006.01)
*A61F 5/01*  (2006.01)

(52) U.S. Cl.
CPC ............... *A61M 25/02* (2013.01); *A61F 5/01* (2013.01); *A61F 5/37* (2013.01); *A61M 2025/028* (2013.01); *A61M 2025/0213* (2013.01)

(58) Field of Classification Search
CPC .......... A61M 25/02; A61F 5/01; A61F 5/012; A61F 5/05816; A61F 5/37; A61F 5/3769
See application file for complete search history.

(56) References Cited

U.S. PATENT DOCUMENTS

| | | | | |
|---|---|---|---|---|
| 2,693,794 A * | 11/1954 | Neville | ........ | A61M 5/52 600/499 |
| 3,242,923 A * | 3/1966 | Jacoby, Sr. | ........ | A61M 5/52 128/877 |
| 3,256,880 A * | 6/1966 | Caypinar | ........ | A61M 5/52 128/877 |
| 4,182,320 A * | 1/1980 | Sweeney | ........ | A61F 5/05816 602/13 |
| 4,502,477 A * | 3/1985 | Lewis | ........ | A61M 25/02 128/879 |
| 4,503,849 A * | 3/1985 | Morgan | ........ | A61M 5/52 128/877 |
| 4,505,270 A * | 3/1985 | Miles | ........ | A61F 5/058 128/877 |

(Continued)

*Primary Examiner* — Kristen Matter

(57) ABSTRACT

A system including method and device with attachments and elements as a means of enhancing vascular access or other medical procedures, such as wound care or diagnostics, or for general medical purposes by effectively stabilizing patients' upper or lower extremities in a safer, more reliable, less intrusive and less costly manner. One embodiment indicates a rigid device with attachments for securing and immobilizing the rigid device and a shape and inflatable pressure cuffs (211) or bands for stabilizing the extremity to the device by eliminating or reducing the number of involved medical personnel, reducing risk of injury or trauma such as medical adhesive related skin injuries or contusions and eliminating or reducing the need for sedation to accomplish the medical procedure especially in children, infants, neonates, and preemies. Other embodiments include multiple sizes, shapes, dimensions, materials and elements necessary to accomplish safe stabilization of an extremity.

3 Claims, 1 Drawing Sheet

(56) References Cited

U.S. PATENT DOCUMENTS

Figure 1:
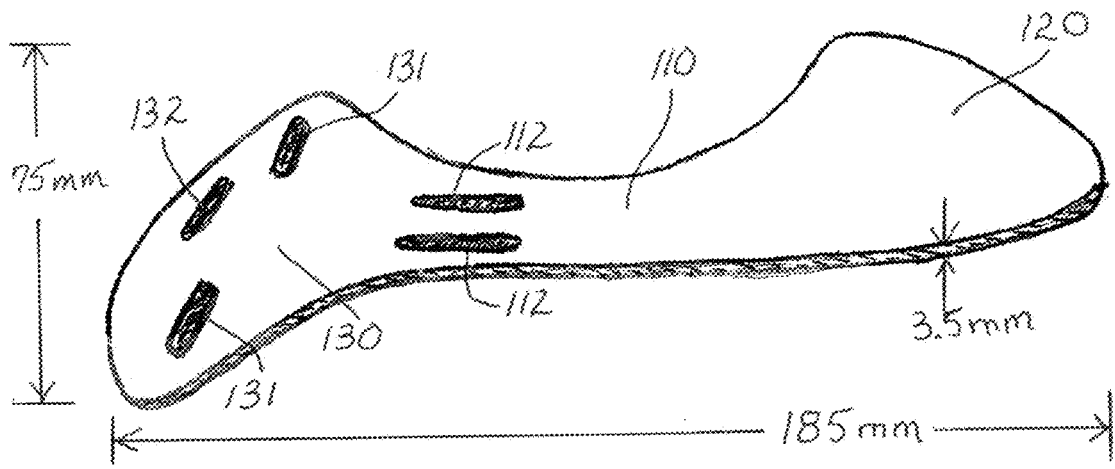

| | | | | |
|---|---|---|---|---|
| 4,798,199 A * | 1/1989 | Hubbard | ............. | A61F 5/05866 |
| | | | | 128/845 |
| 5,263,497 A * | 11/1993 | Grabenkort | .......... | A61B 5/0084 |
| | | | | 128/869 |
| 5,845,643 A * | 12/1998 | Vergano | .............. | A61F 5/05866 |
| | | | | 128/877 |
| 7,182,088 B2 * | 2/2007 | Jenkins | ................... | A61M 5/52 |
| | | | | 128/878 |
| 2009/0192426 A1* | 7/2009 | Ciamillo | ............. | A61F 5/05816 |
| | | | | 602/20 |
| 2011/0100374 A1* | 5/2011 | Silfverskiold | ............ | A61F 5/05 |
| | | | | 128/845 |

\* cited by examiner

EXTREMITY STABILIZATION SYSTEM FOR MEDICAL PROCEDURES

CROSS-REFERENCE TO RELATED APPLICATIONS

This application claims the benefit of provisional application Ser. No. 62/593,459 filed Dec. 1, 2017 by the present inventor, which is incorporated by reference in its entirety.

FEDERALLY SPONSORED RESEARCH nonapplicable.

INCORPORATION BY REFERENCE CD OF SEQUENCE LISTING OR PROGRAM LISTING nonapplicable.

BACKGROUND

Technical Field

The present invention relates to the safe stabilization of the extremity of medical patients especially children, infants, neonates, and preemies allowing vascular access and more particularly for general medical purposes.

Prior Art

It is known in the prior art that medical patients require restraint or stabilization of upper or lower extremities in order to perform vascular access, such as peripherally inserted central catheter (picc) or for other general medical procedure, such as diagnostics and wound care, or for other general medical purposes. The current state of the art or practice is extremely crude and archaic requiring the use of medical abrasives, straps or ties or other restraints directly onto the patient's extremity on one end and to the bed or gurney frame, rail or other relatively non-deformable structure to immobilize the extremity for medical procedures. This method also requires a plurality of medical professionals to acquire such restraint by physically holding the patient down at least at the extremity's proximal end whereby another medical professional may perform the required medical procedure. In most cases, the patient is injected with expensive and potentially dangerous sedation such as ketamine, fentanyl, valium, propofol or other medication that may have residual effects on the general health of the patient.

The current method or prior art is archaic at best and potentially lethal at worst. Manually restraining the patient and attaching straps or medical adhesives directly to the patient's extremities may cause injury to an already critical patient. In many cases, though medical sedation is prescribed to assist in restraining the extremity, the patient may not be able to tolerate the required levels of sedation necessary to restrain the extremity for performing the required medical procedure or may have already received the maximum dosage of sedation. Furthermore, many patients are too young, too small or medically unstable to receive sedation. The current method and procedure suffer from a number of disadvantages:

(a) A plurality of medical personnel are often required to physically immobilize the patient and extremity for vascular access or for general medical purposes. The necessity and presence of additional medical personnel is costly and adds anxiety to the patient receiving the medical procedure.

(b) Medical adhesives, ties, cords or straps to secure the patient's extremity to the bed or gurney frame, rail or other relatively non-deformable structure may cause medical adhesive skin related injuries (MASRI), contusions or other injuries. Medical adhesive skin related injuries may lead to Infection which leads to extended hospitalization and associated risks and costs.

(c) Sedatives such as ketamine, fentanyl, valium, propofol or other medications are costly and may have immediate or residual negative effects on the patient. In some cases, patients reactions to sedation may result in chronic or permanent impairment or even death.

The current methods used in hospitals, intensive care units or other medical facilities are in need of a more patient-safe, patient-friendly system thereby reducing risks and costs.

SUMMARY

In accordance with one embodiment a system as described for stabilizing an upper or lower extremity of a patient for vascular access or for general medical purposes using a less invasive method and a rigid device with the described properties, elements and attachments to substantially improve the comfort and safety to the patient receiving the medical procedure and to potentially reduce health care costs of the medical procedure.

Advantages

Accordingly several advantages of one or more aspects are as follows: to provide a device that is secured to a relatively non-deformable structure on one end and by the natural weight of the patient on the other end whereby the patient's extremity is stabilized to the immobilized rigid device reducing or eliminating stresses and potential injury such as medical adhesive skin related injuries and contusions to the extremity and by reducing the need for additional medical personnel to restrain the patient or unnecessarily requiring the need for medical sedation of the patient in order to perform the medical procedure. Other advantages of one or more aspects will become apparent from consideration of the drawings and ensuing descriptions.

DRAWINGS—FIGURES

FIG. 1 schematically illustrates one embodiment in which a reversible rigid device such as a thin board-like structure with slots for insertion of an inflatable pressure cuff with slots for securing a pneumatic bulb for inflating the pressure cuff, a slot for a strap attached at the distal end for securing and immobilizing the rigid device to a relatively non-deformable structure for subsequent stabilization of the patient's extremity.

Figure 2:
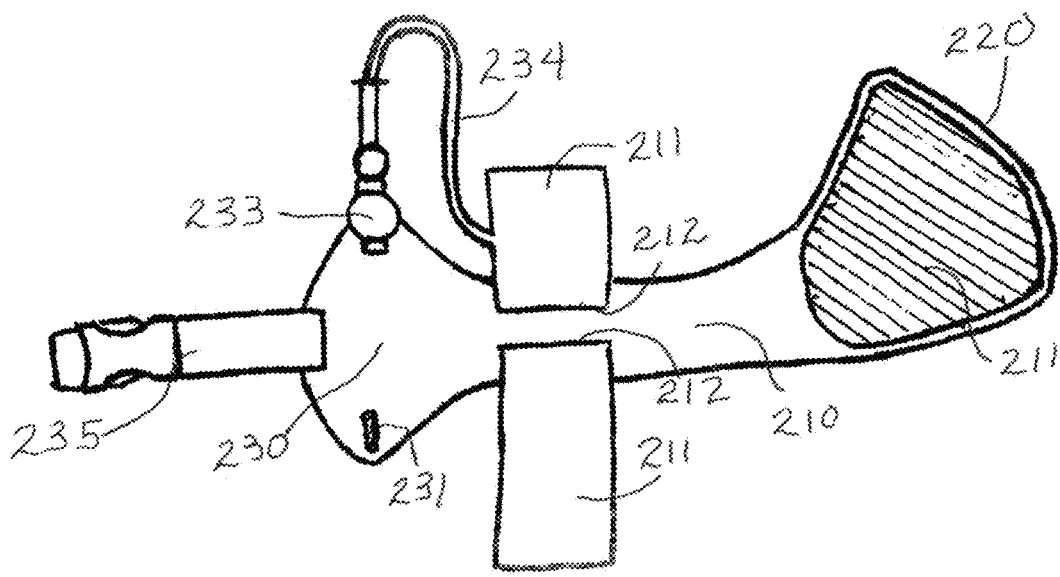

FIG. 2 shows one embodiment of the reversible rigid device of FIG. 1 with a plurality of attachments or elements for securing said rigid device and stabilizing the subject extremity. The attachments or elements are inserted through the slots of the rigid device identified in FIG. 1. One embodiment indicates a non-abrasive cover or coating on the proximal end, an inflatable pressure cuff, a pneumatic bulb and pneumatic tube for inflating said inflatable cuff and straps for securing and immobilizing the rigid device to a relatively non-deformable structure.

| Drawings - Reference Numerals | | |
|---|---|---|
| 10 - rigid device shaft | 11 - inflatable pressure cuff | 12 - slots for pressure cuff |
| 20 - proximal end | 21 - non-abrasive, non-slip covering | |
| 30 - distal end | 31 - slot for pneumatic bulb | 32 - slots for device straps |
| 33 - pneumatic bulb | 34 - pneumatic tube | 35 - device straps |

DETAILED DESCRIPTION OF SPECIFIC EMBODIMENTS

One embodiment of the rigid device is illustrated in the isometric view of FIG. 1. The device shown has a flat board-type structure of uniform thickness composed of a rigid or semi-rigid material with a length and width to sufficiently accommodate the subject patient extremity and a shaft section 110 connecting a proximal end 120 and a distal end 130. One embodiment indicates a nominal length of 185 mm, a nominal width of 75 mm, and a nominal thickness of 3.5 mm. However, the rigid device may come in a plurality of dimensions and shapes depending on the age, size, weight and strength of the patient and the stiffness of the material of the device. The shaft 110 has slots 112 to accept attachments or elements shown in the embodiment of FIG. 2.

In this embodiment the proximal end 120 is oblong shaped to comfortably slide under the shoulder area of the patient for upper extremity stabilization or the buttock/hip area of the patient for lower extremity stabilization. This embodiment is such that the device is reversible to accommodate either right or left extremities by lying the device so that the extended portion of the proximal end 120 may be slid under the patient's shoulder or buttock/hip from either side of the patient.

Also in this embodiment the distal end 130 aligns with the hand or foot end of the patient's extremity. This distal end of this embodiment include a pneumatic bulb slot 131 and device strap slot 132 for the insertion of attachments or elements shown in FIG. 2. The distal end has a shape that simultaneously provides comfort for the patient and ease of operation by the medical professional.

FIG. 2 is a plan view embodiment of FIG. 1 that includes the attachments and elements of said rigid device. A non-abrasive non-slip covering 221 is provided on the oblong-shaped proximal end 220 to enhance the placement of the proximal end 220 under the patient without slipping.

The rigid device shaft 210 is shown in the embodiment of FIG. 2 to include the attachment of an inflatable pressure cuff 211 that is inserted through the pressure cuff slots 212. The pressure cuff 211 and pressure cuff slots 212 may be modified to accommodate the size, weight, age, and strength of the patient.

The distal end 230 in the embodiment of FIG. 2 is shown with attachments and elements. The pneumatic bulb 233 is attached to the distal end in the pneumatic bulb slot 231. The pneumatic bulb 233 is designed so that compressing or pumping inflates the inflatable pressure cuff 211 to the desired pressure for safely and comfortably stabilizing the patient extremity to the rigid device. A pneumatic tube 234 connects the pneumatic bulb 233 to the inflatable pressure cuff 211 for transport of the air pressure provided by compressing or pumping of the pneumatic bulb 233 into the inflatable pressure cuff 211.

Operation—FIG. 2

The proximal end 220 of the rigid device is carefully slid under the shoulder for upper extremity stabilization or the buttock/hip for lower extremity stabilization so that the body weight of the patient immobilizes the proximal end 220. The non-abrasive, non-slip covering 221 contacts the patient to prevent the proximal end from slipping out from under the patient.

Once the proximal end 220 is positioned, the patient's extremity is aligned with the shaft 210 and between the two extensions of the uninflated inflatable pressure cuff 211. The extensions of the uninflated inflatable pressure cuff 211 are attached over the patient's extremity and secured by a Velcro-like material or other binding commonly used in the medical profession. Once the inflatable pressure cuff 211 is securely fastened to itself, the pneumatic bulb 233 is manually pumped and the compressed air from the pneumatic pump 233 is transported by the pneumatic tube 234 to the inflatable pressure cuff 211 until the desired pressure is obtained.

After the patient's extremity is stabilized to the rigid device, the device straps 235 are secured to the bed frame or similar relatively non-deformable structure for final immobilization of said device. Once the device is fully immobilized the patient's extremity is fully stabilized and the intended vascular access or other medical procedure may be accomplished without the aid of additional medical personnel, medical adhesives and sedation. After the vascular access or other medical procedure is accomplished releasing the patient's extremity is accomplished by reversing the steps enumerated in the stabilization process.

ALTERNATIVE EMBODIMENTS

There are various possibilities and options of shapes, dimensions, materials, elements and attachments available relative to the embodiments indicated. The rigid device may be of uniform or variable thickness as well. The embodiments shown provide a general description of the stabilization device, means and methods. For instance, the inflatable pressure cuff 211 may be replaced with a strap or other inflatable or non-inflatable attachment that would achieve stabilization without injury to the patient. Another example could be that an automated inflation mechanism could replace the pneumatic bulb 233 for inflation of the inflatable pressure cuff 211 or other attachment. It is also easily conceivable that the shape of the rigid device and dimensions of the shaft 210, proximal end 220 and distal end 230 could be altered and still provide the same means of stabilization.

Advantages

From the description above, a number advantages of the embodiments and alternative embodiments of the described extremity stabilization system for medical procedures become evident:

(a) The rigid device and attachments allow for a safer method of vascular access or other medical procedure on a patient's extremity by reducing the number or medical personnel required in limited space.

(b) By reducing the number of personnel, the cost, monetary and time, of performing the needed medical procedure is reduced.

(c) By reducing the number of required medical personnel, the anxiety level of the patient is potentially reduced to allow more comfort to the patient and less conflict with the main medical professional conducting the actual procedure.

(d) The design of the rigid device to utilize the patient's own body weight to assist in the immobilization of the device and subsequent stabilization of the extremity provides less anxiety and stress on the patient while accomplishing the benefits of stabilization.

(e) One or a plurality of inflatable pressure cuff(s) securing the patient's extremity to the rigid device without the need for medical adhesives to secure the patient's extremity directly to the bed frame provides a more comfortable means of stabilization and prevents the risks of medical adhesive skin related injuries and contusions.

(f) The placement of the attachments and elements to the rigid device allows for ergonometric and unobstructed access thereby reducing risk of error or injury.

(g) An extremity stabilization method and device reduce or eliminate the need for sedation, thereby reducing the risks of negative long-term or fatal effects on certain patients, especially children, infants, neonates, and preemies and reduces the overall cost of the procedure to the medical provider, insurer and patient.

(h) Immobilizing or restraining the rigid device as a platform for stabilizing the patient's extremity reduces the risk of physical and emotional trauma to the patient.

CONCLUSIONS, RAMIFICATIONS AND SCOPE

Thus, the reader will see that at least one embodiment of the Extremity Stabilization System for Medical Procedures provides a safer, more reliable, more cost-effective means for vascular access or for other general medical procedures, such as wound care, or for other general medical purposes of a patient's extremities.

The above-mentioned specifications should not be construed as limitations on the scope, but rather as an exemplification of one or several embodiments thereof. Other variations of the device are possible. One variation would be an embodiment of the rigid device on its opposite (flip) side where stabilization is accomplished on the opposite upper or lower extremity (left or right). Other variations would be an automatic inflation mechanism for one or a plurality of pressure cuffs or bands. While device dimensions are specified only as that appropriate for the age, size, weight and strength of the patient and stiffness of the material, it is important to envision embodiments of various sizes and shapes that accomplish the same medical purpose. The device described in one embodiment may be of many materials that provide a rigid structure meeting the requirements for use in a medically-sterilized setting. The size, shape, and dimensions are dependent on the age, size, weight, strength or other characteristics of the patient and the stiffness or rigidity of the material selected, and are, therefore, not limited to any arbitrary or non-arbitrary size, shape, or dimension. Rigid device and attachments are not limited to any particular color and may be clear, depending on the material selected. Other embodiments may include a device for use in veterinary-medical setting for non-human veterinary procedures similar to human general medical purposes with the appropriate size, shape, dimensions, materials and elements for veterinary use.

Accordingly, the scope should be determined not by the embodiments illustrated but by the appended claims and their legal equivalents.

That which is claimed:

1. A device configured to stabilize an extremity of a patient during a medical procedure comprising:
    a rigid board having a top surface and a longitudinal axis extending from a proximal end to a distal end of the board, the board having a length configured to substantially match a length of the extremity;
    at least one inflatable cuff secured to the board configured to encircle and secure a distal end of the patient's extremity;
    a pneumatic bulb or pump for pressurizing the at least one inflatable cuff;
    a slot extending through the distal end of the board; and
    a strap extending parallel to the longitudinal axis of the board and through the slot on the distal end, the strap configured for securing the device to a bed frame or bed rail.

2. The device of claim 1, wherein the top surface of the board comprises a non-abrasive, slip-resistant surface configured to contact the patient.

3. A method of stabilizing an extremity of a patient for vascular access comprising:
    providing the device of claim 1;
    placing the board under the extremity of the patient such that extremity is aligned with the longitudinal axis of the board and body weight of the patient immobilizes the proximal end of the board;
    securing the at least one inflatable cuff around the extremity;
    using the pneumatic bulb or pump to inflate the at least one inflatable cuff to a desired pressure; and
    securing the strap to the bed frame or bed rail.

* * * * *